(12) United States Patent
Miller

(10) Patent No.: US 8,986,247 B2
(45) Date of Patent: Mar. 24, 2015

(54) INSUFFLATION PUMP

(76) Inventor: Stuart H. Miller, Clifton, NJ (US)

( * ) Notice: Subject to any disclaimer, the term of this patent is extended or adjusted under 35 U.S.C. 154(b) by 322 days.

(21) Appl. No.: 13/537,891

(22) Filed: Jun. 29, 2012

(65) Prior Publication Data

US 2013/0006176 A1    Jan. 3, 2013

Related U.S. Application Data

(60) Provisional application No. 61/502,596, filed on Jun. 29, 2011.

(51) Int. Cl.
*A61M 29/00* (2006.01)
*A61M 25/10* (2013.01)

(52) U.S. Cl.
CPC .................................. *A61M 25/1018* (2013.01)
USPC ......................................................... 604/97.02

(58) Field of Classification Search
CPC ........... A61M 2005/1403; A61M 2005/14533; A61M 2005/14573; A61B 17/12013; F04B 43/06; F04B 13/00
USPC .............................. 604/6.11, 6.12, 97.02, 223
See application file for complete search history.

(56) References Cited

U.S. PATENT DOCUMENTS

| | | | | |
|---|---|---|---|---|
| 1,698,852 | A | * | 1/1929 | Miller et al. .................... 425/154 |
| 2,074,401 | A | * | 3/1937 | Kauzal ............................ 604/186 |
| 2,773,500 | A | * | 12/1956 | Young ............................. 604/188 |
| 4,737,151 | A | * | 4/1988 | Clement et al. ................ 604/223 |
| 4,808,165 | A | | 2/1989 | Carr |
| 4,976,725 | A | * | 12/1990 | Chin et al. ...................... 606/192 |
| 5,209,731 | A | | 5/1993 | Sterman et al. |
| 5,273,537 | A | | 12/1993 | Haskvitz et al. |
| 5,336,201 | A | | 8/1994 | von der Decken |
| 5,507,727 | A | | 4/1996 | Crainich |
| 5,733,258 | A | * | 3/1998 | Lane ............................... 604/506 |
| 5,830,194 | A | * | 11/1998 | Anwar et al. .................. 604/223 |
| 6,030,368 | A | | 2/2000 | Anwar et al. |
| 7,041,084 | B2 | * | 5/2006 | Fojtik ............................. 604/181 |
| 7,306,574 | B2 | | 12/2007 | Massey et al. |
| 7,527,605 | B2 | | 5/2009 | Evans |
| 7,534,234 | B2 | | 5/2009 | Fojtik |
| 2009/0088702 | A1 | | 4/2009 | Fojtik |
| 2013/0006176 | A1 | * | 1/2013 | Miller ........................ 604/97.02 |

* cited by examiner

*Primary Examiner* — Jason Flick
*Assistant Examiner* — Diva K Chander
(74) *Attorney, Agent, or Firm* — Welsh Flaxman & Gitler LLC

(57) ABSTRACT

An insufflation pump is provided for single handed actuation for inflation of dilatation balloons or other inflatable devices employed during medical procedures. The insufflation pump includes a pump body having a first end and a second end. The first end is provided with a syringe mechanism and the second end is provided with an actuation mechanism. The syringe mechanism and the actuation mechanism are linked by a pivoting mechanical linkage member facilitating the transfer of power from the actuation mechanism to the syringe mechanism. The actuation mechanism includes an actuator pivotally secured adjacent the second end of the pump body. The linkage member includes a first end and a second end, the first end of which is pivotally connected to the second end of the actuator, the second end of the linkage member is pivotally secured to the plunger of the syringe mechanism.

14 Claims, 6 Drawing Sheets

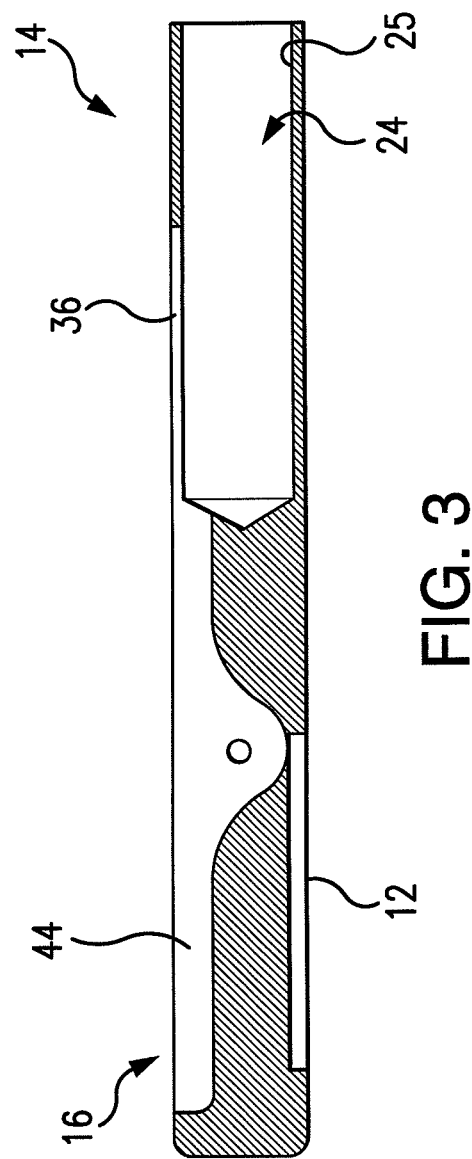

INSUFFLATION PUMP

CROSS REFERENCE TO RELATED APPLICATION

This application claims the benefit of U.S. Provisional Patent Application Ser. No. 61/502,596, entitled "INSUFFLATION PUMP", filed Jun. 29, 2011.

BACKGROUND OF THE INVENTION

1. Field of the Invention

The invention relates to an insufflation pump.

2. Description of the Related Art

Insufflators are devices employed by certain medical specialties, such as Interventional Radiology and Cardiology, for expanding specialized catheters containing inflatable balloons. These balloons containing vascular catheters are typically utilized for a specific purpose, that is, for the performance of angioplasty. Angioplasty is performed to dilate arteries, veins and other closed, tubular structures within the body. These additional structures may include the biliary tree, ureters, kidneys, as well as other tissue which needs to be expanded radially. Most recently, with the advent of Kyphoplasty for the repair of vertebral compression fractures of the spine, balloon catheters have been used to expand compressed bone.

Currently, available insufflators are filled with a mixture of radiopaque contrast material and sterile saline during a procedure. This mixture allows the angioplasty balloon to be observed under fluroroscopy by the operating physician, and its precise location can be directly observed in real time. In addition, the response of the vessel to angioplasty can be monitored indirectly by viewing the form of the angioplasty balloon using fluroroscopy: a narrow balloon suggests a poorly dilated vessel while a fully expanded balloon suggests a successfully dilated vessel.

All available insufflators require two hands for operation: one to hold the body of the insufflator, while the other either activates a screw down device or a plunging type device. Pressure developed, often in atmospheres, may be read by a pressure gauge on the device. A second physician, or technician, is needed to hold the angioplasty catheter in the proper position during the angioplasty procedure and inflation of the balloon. If the angioplasty catheter is not firmly held in position, it can leap forward or backward off the vascular plaque. This results in, as a best-case scenario, inadequate angioplasty due to improper balloon placement, or in the worse scenario, vessel dissection and possible death.

The practice of modern medicine often employs the placement of catheters into the body for various purposes. These might include vascular, peripherally inserted central catheters for short and long term venous access, tunneled catheters for hemodialysis, subcutaneous port-catheters for chemotherapy, and central venous catheters. Catheters are also placed for drainage purposes. This includes, but is not limited to, catheters placed for abscess drainage, catheters placed to drain obstructed kidneys, urinary bladders, gallbladder and biliary systems. Catheters are also placed in the gastrointestinal tract for feeding purposes.

A catheter is simply a hollow plastic tube, or conduit, through which the aforementioned body fluid may pass. The various catheters, as described above, lie in various body locations and drain body fluids, such as blood, bile, urine, and abscess fluid. The outer end of the catheter may be connected to tubing, capped, or connected to various drainage devices. Regardless of the medium into which the catheter is placed or its intended usage, all temporary or permanent catheters must be periodically flushed or drained to ensure proper function and flow; that is, to prevent catheter occlusion from clotted blood and other bodily fluid both in and around the catheter. Certain vascular catheters must be properly flushed to prevent blood clot formation around the catheter which may become life threatening and necessitate the removal and subsequent replacement of the catheter.

The current solution to this problem is to perform scheduled flushing of the catheter, usually with sterile saline. This is accomplished by a nurse partially filling a syringe with saline, then screwing it onto the catheter and then "pulling back" on the syringe to observe flow from the catheter, then flushing it with several cc of sterile saline. With certain catheters, this may need to be performed 3 to 4 times per day. This can become quite labor intensive for hospitalized as well as nursing home patients. In the outpatient setting, it can become quite a time consuming task since a visiting nurse is often needed to tend to daily catheter care.

SUMMARY OF THE INVENTION

It is, therefore, an object of the present invention to provide an insufflation pump allowing for single handed actuation for inflation of dilatation balloons or other inflatable devices employed during medical procedures. The insufflation pump includes a pump body having a first end and a second end. The first end is provided with a syringe mechanism and the second end is provided with an actuation mechanism. The syringe mechanism and the actuation mechanism are linked by a pivoting mechanical linkage member facilitating the transfer of power from the actuation mechanism to the syringe mechanism. The syringe mechanism includes a tube and plunger positioned within the tube for movement therein. The actuation mechanism includes an actuator pivotally secured adjacent the second end of the pump body. The actuator is an elongated member having a first end and a second end. The linkage member includes a first end and a second end, the first end of which is pivotally connected to the second end of the actuator, the second end of the linkage member is pivotally secured to the plunger of the syringe mechanism.

It is also an object of the present invention to provide an insufflation pump wherein the plunger includes a rearwardly directed heel that engages a bottom wall of the tube, stabilizing the plunger and preventing the plunger from becoming askew within the tube.

It is another object of the present invention to provide an insufflation pump wherein the tube is integrally formed with the pump body and includes a distal, first end and a proximal, second end, the distal, first end is closed by the plunger while the proximal, second end includes an outlet port through which fluid is dispensed or withdrawn as the plunger moves between the distal, first end of the tube and the proximal, second end of the tube.

It is a further object of the present invention to provide an insufflation pump wherein the outlet port is shaped and dimensioned for selective attachment to a supply tube for the transfer of fluid to and from the tube.

It is also an object of the present invention to provide an insufflation pump wherein a seal member is positioned about a circumference of the plunger for engagement with an inner wall of the tube preventing fluid from escaping distally of the plunger as it moves within the tube.

It is another object of the present invention to provide an insufflation pump wherein the seal member is seated within a recess formed at a forward end of the plunger.

It is a further object of the present invention to provide an insufflation pump wherein the pump body is provided with an access opening shaped and dimensioned for the passage of the mechanical linkage therethrough, the seal member of the plunger creates a barrier separating the access opening from the fluid and allowing the syringe mechanism to maintain a closed system while permitting the actuation mechanism to link with the plunger for causing movement thereof.

It is also an object of the present invention to provide an insufflation pump wherein the actuator includes the first end including a first arm, the second end including a second arm, and a central section between the first end and the second end, the central section is pivotally secured to the pump body at the second end thereof.

It is another object of the present invention to provide an insufflation pump wherein the actuator is formed with a substantially V-shape allowing it to pivot providing controlled movement of the plunger when either the first end of the actuator or the second end of the actuator is pushed toward the pump body.

It is a further object of the present invention to provide an insufflation pump wherein the central section of the actuator includes a transversely extending pivot arm which is pivotally secured to the pump body via a pivot pin extending between the pivot arm and the second end of the pump body. The second arm at the second end of the actuator includes a transversely extending pivot arm pivotally secured to the linkage member via a pivot pin extending therebetween.

It is also an object of the present invention to provide an insufflation pump wherein the second end of the pump body is provided with a recess shaped and dimensioned for receipt of the actuator as it moves between its retracted position and its compressed position.

It is another object of the present invention to provide an insufflation pump wherein the actuator is shaped to match an outer profile of the pump body and the actuator is formed with a curved cross sectional profile matching the outer profile of the pump body.

It is a further object of the present invention to provide an insufflation pump including a click stop mechanism controlling movement of the actuator permitting a physician to stop forward and/or rearward motion of the plunger at any intermediate location between full forward and full rearward and have the plunger remain in that location until the physician changes it.

It is also an object of the present invention to provide an insufflation pump wherein the click stop mechanism is composed of ridges formed along the exterior surface of the pivot arm of the central section and a click stop beam that extends along the base of the pump body for interaction with the ridges in a manner creating a clicking sound as the actuator is moved.

It is another object of the present invention to provide an insufflation pump wherein the click stop beam is resilient and is fixedly secured to the base of the pump body at its proximal end while the distal end is provided with a protrusion and permitted to move, as such, when the ridges move over the protrusion the click stop beam is bent downwardly allowing movement of the lever with the creation of a slight amount of resistance.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 2 and 3 are respectively a top plan view and a side cross sectional view of the pump body of the insufflation pump shown in FIG. 1.

DESCRIPTION OF THE PREFERRED EMBODIMENTS

Figure 1:
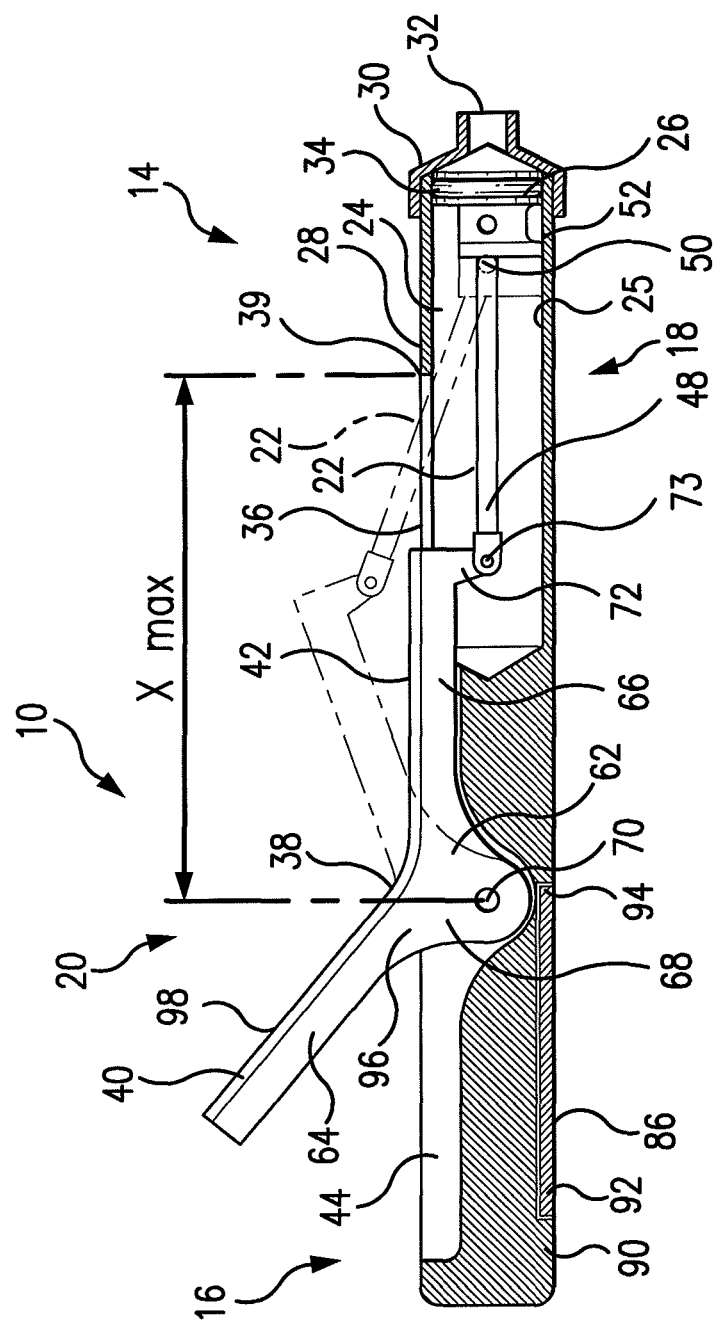
FIG. 1 is a side cross sectional view of the insufflation pump in accordance with the present invention.

The detailed embodiments of the present invention are disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 14, an insufflation pump 10 is disclosed. The insufflation pump 10 allows for single handed actuation for inflation of dilatation balloons and other inflatable devices employed during medical procedures.

The insufflation pump 10 includes a pump body 12 having a first end 14 and a second end 16. The first end 14 is provided with a syringe mechanism 18 and the second end 16 is provided with an actuation mechanism 20. The syringe mechanism 18 and the actuation mechanism 20 are linked by a pivoting mechanical linkage member 22 facilitating the transfer of power from the actuation mechanism 20 to the syringe mechanism 18.

The present invention employs an insufflation pump 10 that contains a plunger 26 of a syringe mechanism 18 attached to a lever system, composed of the actuation mechanism 20 and linkage member 22, which greatly amplifies the mechanical advantage necessary to create the large atmospheric pressures needed for adequate catheter balloon inflation. Once filled with radiopaque contrast and saline, the entire angioplasty process may be performed by a single physician. One hand holds the angioplasty catheter while the other hand is used to activate the insufflation pump 10 of the present invention. In this manner, a more precise, controlled angioplasty may be performed since one person controls both the placement as well as the inflation of the balloon.

First considering the syringe mechanism 18 at the first end 14 of the pump body 12, the syringe mechanism 18 includes a tube 24 and plunger 26 positioned within the tube 24 for movement therein. The tube 24 is integrally formed with the pump body 12 and includes a distal, first end 28 and a proximal, second end 30. The distal, first end 28 is closed by the plunger 26 while the proximal, second end 30 includes an outlet port 32 through which fluid is dispensed or withdrawn as the plunger 26 moves between the distal, first end 28 of the tube 24 and the proximal, second end 30 of the tube 24. The outlet port 32 is shaped and dimensioned for selective attachment to a supply tube 24 for the transfer of fluid to and from the tube 24, that is, between the dilatation catheter and the syringe mechanism 18. The outlet port 32 at the second end 30 of tube 24 is closed by the seal member 34 of plunger 26 when the piston is in its fully extended position adjacent the second end 30 as shown in FIG. 1.

The creation of a sealed environment within the tube 24, in particular, between the outlet port 32 and the plunger 26, is achieved by the provision of a seal member 34 about the circumference of the plunger 26. The seal member 34 is seated within a recess 54 formed at the forward end of the plunger 26. The seal member 34 is shaped and dimensioned to engage the inner wall 25 of the tube 24. As such, fluid is prevented from escaping distally of the plunger 26 as it moves within the tube 24. In addition, and when the outlet port 32 is connected to a dilatation catheter, a closed system is achieved wherein fluid may move between the tube 24 and the dilatation catheter but will not escape the confines of the tube 24 and dilatation catheter. Consequently, when the plunger 26 moves toward the outlet port 32, fluid is forced out of the tube 24 and into the dilatation catheter. When the plunger 26 is moved distally away from the outlet port 32 a vacuum is formed drawing fluid from the dilatation catheter back into the tube 24.

As will be appreciated after reading the following disclosure regarding the actuation mechanism 20, the pump body 12 is provided with an access opening 36 for the mechanical linkage member 22, that is, the access opening 36 is shaped and dimensioned for the passage of the mechanical linkage member 22 therethrough. The access opening 36 would be in fluid communication with the fluid being moved between the tube 24 and the dilatation catheter without the provision of the seal member 34 about the circumference of the plunger 26. However, the seal member 34 of the plunger 26 creates a barrier separating the access opening 36 from the fluid and allowing the syringe mechanism 18 to maintain a closed system while permitting the actuation mechanism 20 to link with the plunger 26 for causing movement thereof.

Figure 4:
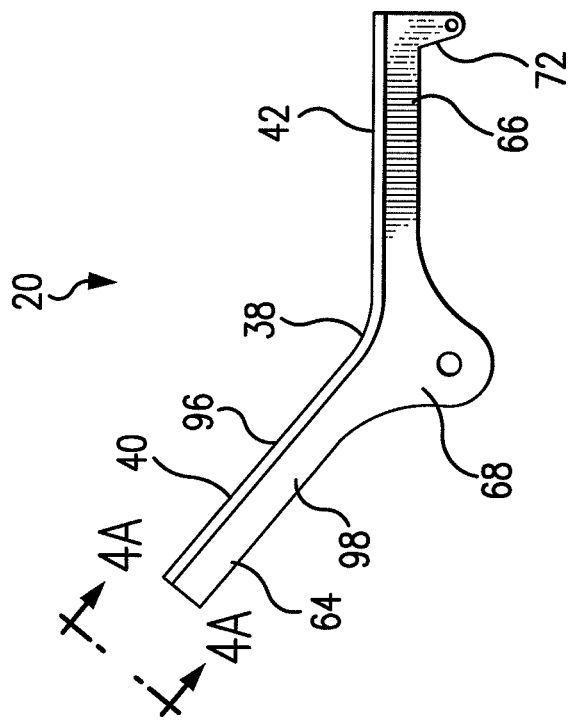
FIG. 4 is a side view of the actuator of the insufflation pump shown in FIG. 1.
Figure 4A:
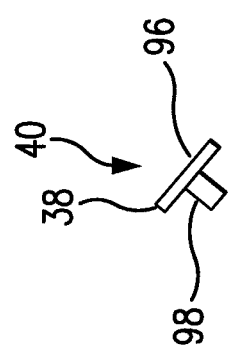
FIG. 4A is a view of the end of the actuator showing the T-shaped construction.
Figure 6:
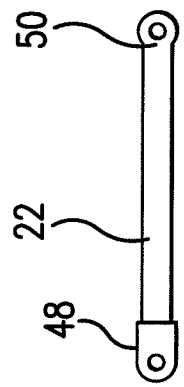
FIGS. 5 and 6 are respectively a top plan view and a side plan view of a lever member of the insufflation pump shown in FIG. 1.
Figure 5:
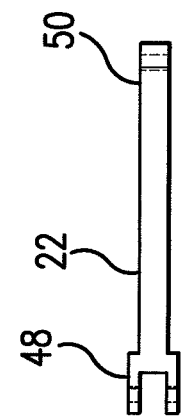
Figure 8:
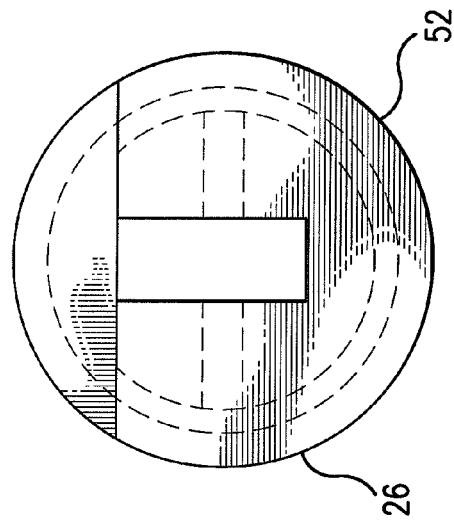
FIGS. 7 and 8 are respectively a side plan view and a rear view of the piston of the insufflation pump shown in FIG. 1.
Figure 10:
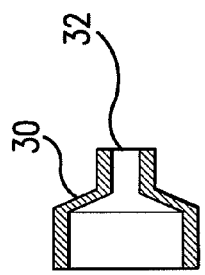
FIGS. 9 and 10 are respectively a cross sectional side view and a rear plan view of the outlet port of the insufflation pump as shown in FIG. 1.
Figure 7:
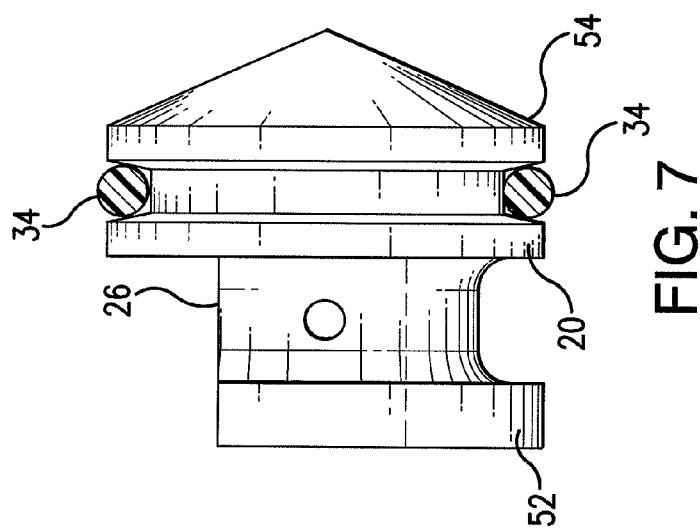
Figure 9:
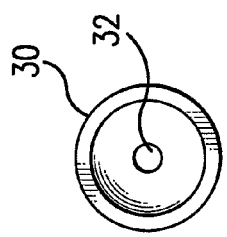

With reference to the second end 16 of the insufflation pump 10, in particular, the actuation mechanism 20, an actuator 38 is pivotally secured adjacent the second end 16 of the pump body 12. The actuator 38 is an elongated member and includes a first end 40 and a second end 42 and a central section 62 between the first end 40 and the second end 42. The central section 62 is pivotally secured to the pump body 12 at the second end 16 thereof. The actuator 38 may be thought of as including a body composed of downwardly extending rib 96 and a flat upper finger engaging surface 98 which extends laterally relative to the downwardly extending rib 96 so as to create a T-shaped cross section (see FIG. 4A). Such a structure imparts rigidity and strength to the actuator.

As will be appreciated based upon the following disclosure, the actuator 38 is formed with a substantially V-shape allowing it to pivot providing controlled movement of the plunger 26 when either the first end 40 of the actuator 38 or the second end 42 of the actuator 38 is pushed toward the pump body 12. The actuator 38 may, therefore, be described as including a first arm 64 having a longitudinal axis and a second arm 66 having a longitudinal axis, wherein the longitudinal axis of the first arm 64 is angularly oriented (that is, not aligned) relative to the longitudinal axis of the second arm 66. In accordance with a preferred embodiment, the longitudinal axis of the first arm 64 is oriented at an angle of 40 degrees relative to the longitudinal axis of the second arm 66. This allows pivoting of the actuator 38 in a manner that raises and lowers the respective first and second ends 40, 42 of the actuator 38 causing movement of the plunger 26 within the tube 24.

More particularly, the central section 62 of the actuator 38 includes a transversely extending pivot arm 68 which is pivotally secured to the pump body 12 via a pivot pin 70 (formed in the rib 98 of the actuator 38) extending between the pivot arm 68 and the second end 16 of the pump body 12. The second end 42 of the actuator 38, that is, the end of the second arm 66, similarly includes a transversely extending pivot arm 72 pivotally secured to the linkage member 22 via a pivot pin 73 extending therebetween.

In order to maintain a low profile as the actuator 38 moves between its retracted position and its compressed position, the second end 16 of the pump body 12 is provided with a recess 44 shaped and dimensioned for receipt of the actuator 38 as it moves between its retracted position and its compressed position. Low profile positioning of the actuator 38 is facilitated by extending the respective pivot arm 72 from the same side of the actuator 38.

Figure 14:
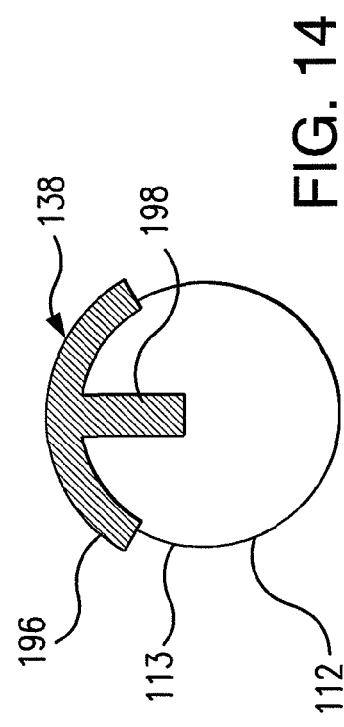
FIG. 14 is a cross sectional view showing the actuator substantially matching the profile of the pump body.

In accordance with an alternate embodiment, and as shown with reference to FIG. 14, the profile of the present device is further improved by shaping the actuator 138 to match the outer profile 113 of the pump body 112. As such, the actuator 138 is formed with a curved cross sectional profile matching the outer profile of the pump body 112. With this in mind, the actuator 138 may be thought of as including a downwardly extending rib 196 and a curved upper finger engaging surface 198 which extends laterally relative to the downwardly extending rib 196 so as to create a substantially T-shaped cross section having a curvature chosen to match the outer profile 113 of the pump body 112.

As stated above, the second end 42 of the actuator 38 is pivotally secured to the linkage member 22. In particular, the linkage member 22 includes a first end 48 and a second end 50, the first end 48 of which is pivotally connected to the second end 42 of the actuator 38. The second end 50 of the linkage member 22 is pivotally secured to the plunger 26 of the syringe mechanism 18. The linkage member 22 is provided with access between the actuator 38, which is located substantially along the exterior of the pump body 12, and the plunger 26, which is located within the pump body 12 in the tube 24 of the syringe mechanism 18. Access is achieved by the provision of an access opening 36 within the pump body 12. The access opening 36 extends from the exterior of the pump body 12 to the interior of the pump body 12 such that it creates a passageway from the actuator 38 to the rear side of the plunger 26.

In this way, movement of the actuator 38, that is, movement of the first end 40 of the actuator 38, that is, the first arm 64, toward and away from the pump body 12 by respectively pressing upon the first arm 64 and the second arm 66 of the actuator 38, will cause the plunger 26 of the syringe mechanism 18 to move between a distal and a proximal position for dispensing fluid to or withdrawing fluid from the dilatation balloon.

Figure 11:
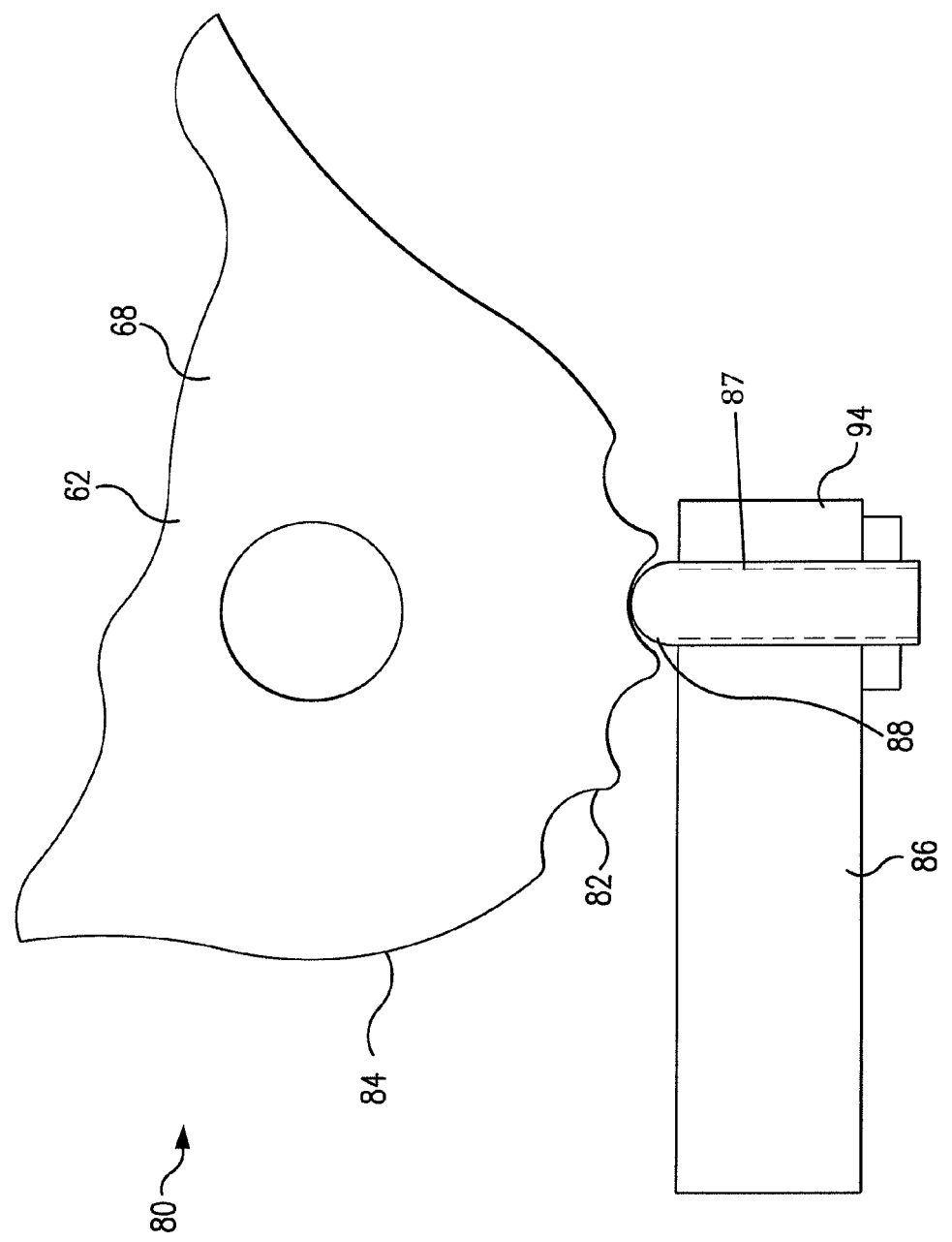
FIG. 11 is a detailed view of the actuator showing the click stop mechanism.
Figure 12:
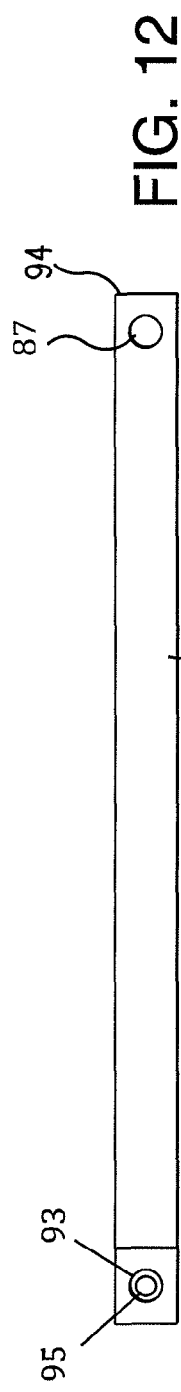
FIGS. 12 and 13 are respectively a top plan view and a side plan view of a click stop beam of the click stop mechanism disclosed with reference to FIG. 10.
Figure 13:
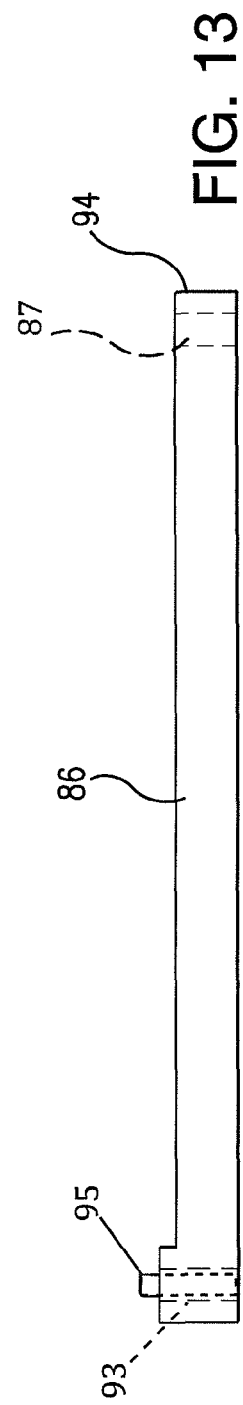

Referring to FIGS. 11, 12 and 13, the actuator 38 is provided with structure permitting controlled movement thereof. In particular, controlled movement of the actuator 38 is achieved through the provision of a click stop mechanism 80. The click stop mechanism 80 is composed of ridges 82 formed along the exterior surface 84 of the pivot arm 68 of the central section 62 and a click stop beam 86 that extends along the base 90 of the pump body 12 for interaction with the ridges 82 in a manner creating a clicking sound as the actuator 38 is moved under the control of the interaction between the ridges 82 along the exterior surface 84 of the pivot arm 68 and the click stop beam 86. The click stop beam 86 is resilient and is fixedly secured to the base 90 of the pump body 12 at its proximal end 92. The proximal end 92 is therefore provided with an aperture 93 for receiving a coupling member 95 that couples the proximal end 92 of the click stop beam 86 to the pump body 12. The distal end 94 of the click stop beam 86 is permitted to move and is provided with an aperture 87 in which a protrusion 88 is positioned. As such, when the ridges 82 move over the protrusion 88, the click stop beam 86 is bent downwardly allowing movement of the actuator 38 with the creation of a slight amount of resistance.

Through use of this embodiment, rather than fully discharging the syringe mechanism 18 (for example, an entire 5 ml load that might be carried by the syringe mechanism) at one time, the physician may prefer to use only a partial discharge. This is achieved by the provision of the ridges 82 along the exterior surface 84 of the pivot arm 68 of the actuator 38 and a click stop beam 86 which is fastened to the underside of the pump body 12 so that the click stop beam 86 provides intermediate stops for the actuator 38. As the actuator 38 is depressed, the click stop beam 86 is deflected into and out of the ridges (or cavities) 82 on the actuator 38. The click stop beam 86 will also maintain the desired position of the actuator 38 for a period of time, and the physician may then discharge additional fluid out of the insufflation pump 10 or poll some of the discharged fluid back into the insufflation pump 10 by simply rotating the actuator 38 clockwise or counterclockwise.

FIG. 11 only shows three stop portions in the actuator travel. Obviously, additional stops may be provided which will permit an increased number of stop locations during the fluid discharge.

It is also appreciated that although a click stop mechanism is disclosed with reference to a preferred embodiment of the present invention, the insufflation device may be constructed without the click stop mechanism where it is determined such a mechanism would be unnecessary or detrimental.

Controlled movement of the plunger 26 within the tube 24 is further facilitated by the shape of the plunger 26. In particular, and because of the linkage arrangement employed in accordance with the present invention, forward pressure (when viewed as shown in FIG. 1) is applied to the plunger 26 as the user presses downwardly upon the actuator 38. In addition to the forward force being applied to the plunger 26, which causes the plunger 26 to move toward the output port, the linkage member 22 applies downward pressure to the plunger 26. This downward pressure might cause misalignment of the plunger 26 within the tube 24, but the plunger 26 is provided with a rearwardly directed heel 52 that engages the bottom wall of the tube 24. The support provided by the heel 52 stabilizes the plunger 26 and prevents the plunger 26 from becoming askew within the tube 24.

In operation, the insufflation pump 10 is operated by depressing the first end 40 or the second end 42 of the actuator 38 toward the pump body 12. As shown in FIG. 1, the plunger 26 is in the fully forward position and the insufflation pump is empty, i.e., it does not contain any fluid. As shown in FIG. 1, a portion of the linkage member 22 is shown in the position which defines the maximum length of the access opening (or slot) 36 from the pivot of the actuator 38 to the location where the upper edge 39 of the linkage member 22 contacts the inner wall of the cavity defined by tube 24 (shown as $X_{imax}$ in FIG. 1). The length of the pump body from $X_{imax}$ to the end of the inside diameter of the pump body 12 is the syringe portion of the pump body 12, i.e., it defines the maximum axial travel of the plunger 26 and the maximum capacity of the syringe portion. It is appreciated the extent of the plunger 26 movement within the pump body 12 is controlled by relative lengths of the members making up the linkage assembly and may, therefore, be adjusted to suit various size constraints.

As shown in FIG. 1, the insufflation pump 10 is empty. To draw a liquid, such as saline, for example, into the insufflation pump 10, the first end 40 of the actuator 38 is depressed until it contacts the pump body 12. This draws a predetermined quantity (for example, 5 ml) of the saline into the syringe mechanism 18 of the pump body 12. Depressing the second end 42 of the actuator 38 downward until it contacts the pump body 12 discharges all of the fluid from the insufflation pump 10.

It should be noted, in an alternate embodiment, that the syringe end of the insufflation pump may be such that 5 ml, for example, saline cartridges may be loaded into the insufflation pump by merely depressing the actuator and drawing the plunger to its maximum retracted position. Depressing the actuator will then discharge the fluid from the cartridge into attached tubing preferably secured thereto via a luer lock.

The present insufflation pump may also be employed for easy and accurate catheter flushing that, in many cases, can be easily accomplished by nurses, nurses' aides, and even the patient in many instances. The insufflation pump is a small, sterile, prefilled device for single use that can be easily placed and deployed. The insufflation pump is removed from the package and a small amount of saline is discharged using the actuator. After wiping with a sterile wipe, the insufflation pump is connected to the catheter. A small amount of fluid residing in the catheter is then withdrawn from the catheter. Any air bubbles should be removed using current techniques. On the down stroke motion of the actuator, the sterile saline prepackaged in the insufflation pump is forward flushed into the catheter. The device is then removed and discarded.

It is appreciated the insufflation pump may be molded, for example, from General Electric HP or any other plastic suitable for medical devices. The enclosed sketches show an "o" ring seal on the piston. This was selected for prototyping purposes and may be replaced by conventional syringe piston seals.

The insufflation pump described herein can be used as a relatively low pressure flushing device. With some modifications, such as the addition of a pressure gauge and overall strengthening of the structure, the basic flusher concept may also be used to inflate balloons.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An insufflation pump allowing for single handed actuation for inflation of dilatation balloons or other inflatable devices employed during medical procedures, comprising:
   a pump body having a first end and a second end, the first end is provided with a syringe mechanism and the second end is provided with an actuation mechanism, the syringe mechanism and the actuation mechanism are linked by a pivoting mechanical linkage member facilitating the transfer of power from the actuation mechanism to the syringe mechanism;
   the syringe mechanism includes a tube and plunger positioned within the tube for movement therein;
   the actuation mechanism includes an actuator pivotally secured adjacent the second end of the pump body, the actuator is an elongated member having a first end and a second end;

the linkage member includes a first end and a second end, the first end of which is pivotally connected to the second end of the actuator, the second end of the linkage member is pivotally secured to the plunger of the syringe mechanism;

further including a click stop mechanism controlling movement of the actuator permitting a physician to stop forward and/or rearward motion of the plunger at any intermediate location between full forward and full rearward and have the plunger remain in that location until the physician changes it.

2. The insufflation pump according to claim 1, wherein the plunger includes a rearwardly directed heel that engages a bottom wall of the tube, stabilizing the plunger and preventing the plunger from becoming askew within the tube.

3. The insufflation pump according to claim 1, wherein the tube is integrally formed with the pump body and includes a distal, first end and a proximal, second end, the distal, first end is closed by the plunger while the proximal, second end includes an outlet port through which fluid is dispensed or withdrawn as the plunger moves between the distal, first end of the tube and the proximal, second end of the tube.

4. The insufflation pump according to claim 3, wherein the outlet port is shaped and dimensioned for selective attachment to a supply tube for the transfer of fluid to and from the tube.

5. The insufflation pump according to claim 3, wherein a seal member is positioned about a circumference of the plunger for engagement with an inner wall of the tube preventing fluid from escaping distally of the plunger as it moves within the tube.

6. The insufflation pump according to claim 5, wherein the seal member is seated within a recess formed at a forward end of the plunger.

7. The insufflation pump according to claim 1, wherein the pump body is provided with an access opening shaped and dimensioned for the passage of the mechanical linkage therethrough, the seal member of the plunger creates a barrier separating the access opening from the fluid and allowing the syringe mechanism to maintain a closed system while permitting the actuation mechanism to link with the plunger for causing movement thereof.

8. The insufflation pump according to claim 1, wherein the actuator includes the first end including a first arm, the second end including a second arm, and a central section between the first end and the second end, the central section is pivotally secured to the pump body at the second end thereof.

9. The insufflation pump according to claim 8, wherein the actuator is formed with a substantially V-shape allowing it to pivot providing controlled movement of the plunger when either the first end of the actuator or the second end of the actuator is pushed toward the pump body.

10. The insufflation pump according to claim 9, wherein the central section of the actuator includes a transversely extending pivot arm which is pivotally secured to the pump body via a pivot pin extending between the pivot arm and the second end of the pump body, the second arm at the second end of the actuator includes a transversely extending pivot arm pivotally secured to the linkage member via a pivot pin extending therebetween.

11. The insufflation pump according to claim 1, wherein the second end of the pump body is provided with a recess shaped and dimensioned for receipt of the actuator as it moves between its retracted position and its compressed position.

12. The insufflation pump according to claim 11, wherein the actuator is shaped to match an outer profile of the pump body and the actuator is formed with a curved cross sectional profile matching the outer profile of the pump body.

13. The insufflation pump according to claim 1, wherein the click stop mechanism is composed of ridges formed along an exterior surface of a pivot arm of a central section of the actuator and a click stop beam that extends along the base of the pump body for interaction with the ridges in a manner creating a clicking sound as the actuator is moved.

14. The insufflation pump according to claim 13, wherein the click stop beam is resilient and is fixedly secured to the base of the pump body at a proximal end while a distal end is provided with a protrusion and permitted to move, as such, when the ridges move over the protrusion the click stop beam is bent downwardly allowing movement of a lever with the creation of a slight amount of resistance.

\* \* \* \* \*